United States Patent
Koch et al.

(10) Patent No.: US 12,029,571 B2
(45) Date of Patent: Jul. 9, 2024

(54) METHODS AND DEVICES FOR PROVIDING A PARAMETER THAT INDICATES A HIGHER LIKELIHOOD OF A POSTOPERATIVE DELIRIUM OCCURRING

(71) Applicant: Covidien LP, Boulder, CO (US)

(72) Inventors: Susanne Koch, Berlin (DE); Claudia Spies, Berlin (DE)

(73) Assignee: COVIDIEN LP, Mansfield, MA (US)

(*) Notice: Subject to any disclaimer, the term of this patent is extended or adjusted under 35 U.S.C. 154(b) by 746 days.

(21) Appl. No.: 17/252,113

(22) PCT Filed: Jun. 17, 2019

(86) PCT No.: PCT/EP2019/065832
§ 371 (c)(1),
(2) Date: Dec. 14, 2020

(87) PCT Pub. No.: WO2019/238974
PCT Pub. Date: Dec. 19, 2019

(65) Prior Publication Data
US 2021/0321928 A1 Oct. 21, 2021

(30) Foreign Application Priority Data
Jun. 15, 2018 (DE) .......................... 102018114364.8

(51) Int. Cl.
*A61B 5/374* (2021.01)
*A61B 5/00* (2006.01)
(Continued)

(52) U.S. Cl.
CPC ............ *A61B 5/374* (2021.01); *A61B 5/7271* (2013.01); *G16H 10/60* (2018.01); *G16H 50/70* (2018.01); *G01R 23/15* (2013.01); *G16H 50/20* (2018.01)

(58) Field of Classification Search
CPC ..... A61B 5/374; A61B 5/4821; A61B 5/7278; A61B 5/7235; A61B 5/7242; A61B 5/7271
See application file for complete search history.

(56) References Cited

U.S. PATENT DOCUMENTS

| 4,846,190 A | 7/1989 | John |
| 2012/0165696 A1* | 6/2012 | Arns ................. A61B 5/4833 600/545 |

(Continued)

FOREIGN PATENT DOCUMENTS

WO    2019145748 A2    8/2019

OTHER PUBLICATIONS

Palanca, et.al. Electroencephalography and delirium in the postoperative period. British Journal of Anaesthesia. Aug. 1, 2017; vol. 119(2): pp. 294-307. doi:10.1093/bja/aew475. (Year: 2017).*

(Continued)

*Primary Examiner* — Eric F Winakur
(74) *Attorney, Agent, or Firm* — Fletcher Yoder, P.C.

(57) ABSTRACT

The invention relates to methods and devices for providing parameters that indicate a higher likelihood of a postoperative delirium occurring. According to a first aspect of the invention, the following steps are provided: detecting (401) at least one EEG signal at the head of the patient; determining (402) the intraoperative alpha peak frequency of the EEG signal, wherein the alpha peak frequency in the power spectrum of the EEG signal is the frequency in the alpha band for which the power is greatest; checking (403) whether the determined intraoperative alpha peak frequency is significantly lower than a predefined reference value of the alpha peak frequency; and in the event of this, providing (404) a corresponding information in the form of a parameter that shows a higher likelihood of a postoperative delirium occurring. A second aspect of the invention evalu- (Continued)

ates the change in power of the alpha band after an anesthetic-inducing drug has been administered. A third aspect of the invention relates to determining the average amplitude of the "direct current" EEG signal and the development of same on initiation of anesthetic-induced loss of consciousness.

20 Claims, 9 Drawing Sheets

(51) Int. Cl.
$$\begin{array}{ll} G01R\ 23/15 & (2006.01) \\ G16H\ 10/60 & (2018.01) \\ G16H\ 50/20 & (2018.01) \\ G16H\ 50/70 & (2018.01) \end{array}$$

(56) References Cited

U.S. PATENT DOCUMENTS

| | | |
|---|---|---|
| 2015/0080754 A1 | 3/2015 | Purdon et al. |
| 2015/0126891 A1* | 5/2015 | Scheib .................. A61B 5/165 600/544 |
| 2016/0045128 A1 | 2/2016 | Sitt et al. |
| 2016/0228028 A1 | 8/2016 | Van der kooi et al. |
| 2016/0324446 A1 | 11/2016 | Prerau et al. |
| 2019/0142336 A1 | 5/2019 | Purdon et al. |
| 2019/0216389 A1 | 7/2019 | Scheib |

OTHER PUBLICATIONS

Hight, et.al. Changes in Alpha Frequency and Power of the Electroencephalogram during Volatile-Based General Anesthesia. Frontiers in Systems Neuroscience. May 29, 2017; vol. 11:36. doi:10.3389/fnsys.2017.00036. (Year: 2017).*

Giattino et al., "Intraoperative Frontal Alpha-Band Power Correlates with Preoperative Neurocognitive Function in Older Adults," Frontiers in Systems Neuroscience, vol. 11, Article 24, May 8, 2017, 11 pp.

Kreuzer, "EEG Based Monitoring of General Anesthesia: Taking the Next Steps," Frontiers in Computational Neuroscience, vol. 11, Article 56, Jun. 2017, 7 pp.

Gaskell et al., "Modulation of frontal EEG alpha oscillations during maintenance and emergence phases of general anaesthesia to improve early neurocognitive recovery in older patients: protocol for a randomised controlled trial," Trials, vol. 20, Feb. 2019, 11 pp.

Fritz et al., "Intraoperative Electroencephalogram Suppression Predicts Postoperative Delirium," Anesth. Analg. vol. 122, Jan. 2016, 18 pp.

Deiner et al., "Can Intraoperative Processed EEG Predict Postoperative Cognitive Dysfunction in the Elderly?", Clinical Therapeutics, vol. 37, No. 12, Dec. 2015, pp. 2700-2705.

Purdon et al., "Electroencephalogram signatures of loss and recovery of consciousness from propofol," Proceedings of the National Academy of Sciences, vol. 110, No. 12, Mar. 4, 2013, pp. 1142-1151.

Smith et al., "Anesthetic Technique (Sufentanil Versus Ketamine Plus Midazolam) and Quantitative Electroencephalographic Changes After Cardiac Surgery," Journal of Cardiothoracic and Vascular Anesthesia, vol. 20, No. 4, Apr. 2006, 9 pp.

Plaschke et al., "Early postoperative delirium after open-heart cardiac surgery is associated with decreased bispectral EEG and increased cortisol and interleukin-6," Intensive Care Med, vol. 36, Aug. 6, 2010, pp. 2081-2089.

International Preliminary Report on Patentability, and English translation thereof, from International Application No. PCT/EP2019/065832, dated Dec. 15, 2020, 26 pp.

International Search Report and Written Opinion, and English translation thereof, from International Application No. PCT/EP2019/065832, dated Sep. 18, 2019, 30pp.

Gu et al. "Integrative Frequency Power of EEG Correlates with Progression of Mild Cognitive Impairment to dementia in Parkinson's Disease," Clinical EEG and Neuroscience, vol. 27, No. 2, Apr. 2016, pp. 113-117.

Radtke et al., "Monitoring depth of anesthesia in a randomized trial decreases the rate of postoperative delirium but hot postoperative cognitive dysfunction," British Journal of Anaesthesia, vol. 110, Supp. Issue 1, Jun. 1, 2013, pp. i98-i105.

* cited by examiner

METHODS AND DEVICES FOR PROVIDING A PARAMETER THAT INDICATES A HIGHER LIKELIHOOD OF A POSTOPERATIVE DELIRIUM OCCURRING

This application is a U.S. National Stage entry under 35 U.S.C. § 371 of International Application No. PCT/EP2019/065832, filed Jun. 17, 2019, which claims priority to German Patent Application No. DE 10 2018 114 364.8, filed on Jun. 15, 2018.

The invention relates to methods and devices for providing a parameter that indicates a heightened likelihood of postoperative delirium occurring.

Postoperative delirium (POD) is a common postoperative complication that is common especially in older people and leads to a prolonged hospital stay, cognitive ability losses, a decline in quality of life after the operation and to increased mortality up to one year after the operation. Predicting which patients have a higher risk of developing POD is carried out by evaluating risk profiles (higher age, reduced cognitive abilities before the operation, etc.). However, the creation of a risk profile is less specific and does not cope with the actual individual risk to the individual patients.

Deducing brainwaves by means of surface electrodes as part of electroencephalography (EEG) was described for the first time at the start of the last century. The EEG oscillations, in which the focus was mainly on epileptic potential, categorizing sleep stages, and assessing coma depth in order to establish brain death, were initially evaluated visually. Adopting computer-based EEG analysis software has considerably improved the evaluation and significance of the findings. The use of EEG data for controlling anesthesia represents a conventional measure.

In electroencephalography, different EEG frequency bands are distinguished. Within the context of the present patent application, the following definitions are used for the EEG frequency bands: direct current EEG: <0.5 Hz; sub-delta Band: 0.5-1.5 Hz; delta band: 1.5 to 4 Hz; theta band: 4 to <8 Hz; alpha band: 8 to 12 Hz; beta band: >12 to 35 Hz and gamma band: >35 Hz.

Furthermore, it is known to characterize the individual alpha frequency by determining the alpha peak frequency (aFP). This is the frequency in the alpha band having the highest power, i.e. in the power spectrum of an EEG signal, this is the frequency at which the power or the square amplitude is maximal in the alpha band. Gu Y, Chen J, Lu Y, Pan S.:

"Integrative Frequency power of EEG correlates with progression of mild cognitive impairment to dementia in Parkinson's disease," Clin EEG Neurosci. 2016; 47 (2): 113-117, report that the alpha peak frequency correlates with cognitive abilities.

F. M. Radtke, M. Franck, J. Lendner, S. Kruger, K. D. Wernecke, C. D. Spies: "Monitoring depth of anesthesia in a randomized trial decreases the rate of postoperative delirium but not postoperative cognitive dysfunction," BJA: British Journal of Anaesthesia, Volume 110, issue suppl_1, 1 Jun. 2013, pages i98-i105 describe that the postoperative delirium rate can be significantly reduced by an EEG-assisted neuromonitoring of the depth of anesthesia. In this case, the depth of anesthesia is measured by means of an EEG evaluation in order to carry out the anesthesia procedure more accurately and to thereby be able to reduce the postoperative delirium rate.

The object of the present invention is to provide methods and devices that provide information that allow a doctor or anesthetist to estimate the likelihood of postoperative delirium occurring.

This object is achieved by a method having the features of claim 1, a method having the features of claim 11, a method having the features of claim 20, a device having the features of claim 26, a device having the features of claim 35 and a device having the features of claim 44. Embodiments of the invention are stated in the dependent claims.

In a first aspect, the invention then provides a method for providing a parameter that indicates a heightened likelihood of postoperative delirium occurring. According to the method, at least one EEG signal is recorded on the patient's head. The intraoperative alpha peak frequency of the EEG signal is determined, in which the alpha peak frequency in the power spectrum of the EEG signal is the frequency in the alpha band at which the power is greatest. Furthermore, a check is made to see whether the intraoperative alpha peak frequency determined is significantly (i.e., in a defined manner) lower than a preset reference value for the alpha peak frequency. As will be explained, the reference value is an average alpha peak frequency for a reference group of patients that have not developed postoperative delirium, for example.

In the event that the intraoperative alpha peak frequency is significantly lower than the preset reference value, a corresponding piece of information is provided as a parameter, in which the parameter indicates a heightened likelihood of postoperative delirium occurring.

The parameter can be used by a doctor in conjunction with other parameters to decide whether the patient will be therapeutically treated at an early stage.

It should be noted that the step of checking whether the intraoperative alpha peak frequency is significantly lower than a preset reference value for the alpha peak involves creating a difference between the preset reference value and the intraoperative alpha peak frequency. Provided that this difference meets specific criteria, i.e. it is greater than a preset value, the intraoperative alpha peak frequency is "significantly" lower than a preset reference value. Furthermore, it should be noted that the parameter indicating a heightened likelihood of postoperative delirium occurring likewise consists in indicating that the intraoperative alpha peak frequency is significantly lower than the preset reference value.

It should also be noted that the step of checking to see whether the intraoperative alpha peak frequency determined is significantly lower than a preset reference value can be carried out by machine learning according to one variant of the invention, in which an artificial system learns from examples of a significantly lower intraoperative alpha peak frequency and can generalize these examples after the learning phase has ended, in which patterns and regularities are recognized in the learning data.

The invention relates to the surprising knowledge that a parameter can be provided by means of the alpha peak frequency, which is to be determined intraoperatively, or the deviation thereof from a reference value, by means of which parameter the development of postoperative delirium can be predicted or at least estimated more effectively. This allows for early therapeutic intervention, after which the occasionally fatal complications in patients suffering from postoperative delirium could be prevented or reduced.

Since this relates to a device-based examination, which can also be easily implemented in routine clinical practice, the invention can considerably increase diagnostic reliability. According to the invention, a warning can be given as early as during the operation so that supportive therapeutic measures can be taken. In the recovery room and the further care station the patient can also be correspondingly treated or further progress can be monitored carefully.

One embodiment of the invention provides that the preset reference value has been established by averaging the intraoperative alpha peak frequencies measured for a plurality of patients who have not developed postoperative delirium. In this case, the reference value may be preset on the basis of the age bracket of the patient. Therefore, for example, a first reference value is established for a first age bracket (for example 65-70 years), whereby the intraoperative alpha peak frequencies measured in a plurality of patients in this first age bracket are averaged. A second reference value is established for a second age bracket (for example 70-80 years), whereby the intraoperative alpha peak frequencies measured in a plurality of patients in this second age bracket are averaged. By selecting the reference value on the basis of a specific age bracket, the likelihood of the correct prediction of postoperative delirium occurring is improved. However, it should be pointed out that determining the reference value on the basis of the age bracket is just one embodiment of the invention.

In additional embodiments, the preset reference value can be established by taking into consideration the intraoperative alpha peak frequencies measured for a plurality of patients that have not developed postoperative delirium, and additionally by taking into consideration the intraoperative alpha peak frequencies measured for a plurality of patients that have developed postoperative delirium. As a result, the typical frequency spacing of the alpha peak frequency between patients that develop postoperative delirium and patients that do not develop postoperative delirium can be taken into consideration when determining the reference value.

Another embodiment of the invention provides that the intraoperative alpha peak frequency is determined at a point in time at which the patient is in a stable state of anesthesia. For example, the intraoperative alpha peak frequency is measured 15 minutes after intubation or after consciousness has been lost. However, these values are only to be understood by way of example.

In this case, the intraoperative alpha peak frequency of the patient can be repeatedly measured across a defined intraoperative period of time and an average created.

As explained, according to the method according to the invention, a check is made to see whether the intraoperative alpha peak frequency is significantly lower than a preset reference value for the alpha peak frequency and, if so, a corresponding piece of information is output as a parameter. The alpha peak frequency lies significantly lower, for example, whether the difference between the preset reference value and the intraoperative alpha peak frequency exceeds a defined percentage deviation from the reference value or a defined absolute difference between the intraoperative alpha peak frequency and the reference value. In the first case, for example, a check is made to see whether the intraoperative alpha peak frequency deviates at least X %, for example at least 10%, from the reference value. In the second case, for example, a check is made to see whether the frequency difference between the intraoperative alpha peak frequency and the reference value exceeds a predefined value, for example 1 hertz.

According to the invention, a frontal EEG signal is preferably picked up, i.e., a frontal deduction is carried out in which the EEG signal is measured at at least two electrodes that are arranged in different places on the patient's forehead. In this case, a plurality of frontal EEG signals may be picked up that are averaged in order to determine the alpha peak frequency. In the 10-20 system typically used, signals are derived from electrodes that are positioned in positions F7, F8, Fp1, Fp2 and Fpz, for example.

A bipolar deduction (difference between two active electrodes) or a unipolar deduction (difference between a plurality of active electrodes against a common reference) can occur.

Another embodiment provides that the intraoperative alpha peak frequency of the EEG signal is determined after this has been filtered through a band-pass filter. The band-pass filter is formed, for example, such that it only allows signal in the frequency range of from 0.5-40 Hz to pass through.

Another embodiment provides that, when determining the intraoperative alpha peak frequency of the EEG signal, the frequency at which the power in the power spectrum of the EEG signal in the alpha band and theta band is greatest is determined. Although the alpha peak activation is usually in the alpha band during operation, in patients that develop postoperative delirium after the operation (POD patients), the peak frequency can also be in the upper theta band, wherein the theta band stretches between 4 and 8 Hz. Such a frequency peak that lies in the upper theta band will also be referred to as an alpha peak within the context of the present invention.

In a second aspect, the invention provides a method for providing another parameter that indicates a heightened likelihood of postoperative delirium occurring. According to the method, at least one EEG signal is recorded on the patient's head. The power of the alpha band of the EEG signal is determined, in which the power of the alpha band in the power spectrum of the EEG signal is defined as the integral of the power across all the frequencies in the alpha band. The power of the EEG signal across all the frequencies in the alpha band is therefore determined.

Therefore, a first power of the alpha band is determined at a preoperative point in time before an anesthetic-inducing medication is administered, and a second power of the alpha band is determined at an intraoperative point in time that is after entering the anesthetic-induced loss of consciousness. A check is then made to see whether an increase in the power of the alpha band from the first power to the second power is below a predefined amount. If so, a corresponding piece of information is provided as a parameter indicating heightened likelihood of postoperative delirium occurring.

The second aspect of the invention firstly is based on the basic fact that, during anesthesia, the power of the alpha band increases. This therefore relates to the fact that alpha activation occurs as a result of the intraoperative activation of the GABA neurons in the frontal region. The invention has now revealed the surprising connection that the power of the alpha band in patients that develop postoperative delirium increases under anesthetic to a smaller extent than in patients that do not develop postoperative delirium. In other words, in patients that develop postoperative delirium, the increase in the power of the alpha band from the first power (preoperative) to the second power (intraoperative) is below a predefined amount (which, in extreme cases, also includes the power of the alpha band even decreasing from the preoperative to the intraoperative state).

It should be pointed out that, according to one design variant of the invention, the check to see whether an increase in the power of the alpha band from the first power to the second power is below a predefined amount can be carried out by machine learning, in which an artificial system learns from examples of a reduced increase in the power of the alpha band and can generalize these examples after the learning phase has ended, in which patterns and regularities are recognized in the learning data.

In the second aspect of the invention, too, the diagnosis reliability can be considerably increased since this aspect relates to an appliance-based study that can also be easily implemented in routine clinical practice. A warning can be issued as early as during the operation so that supportive therapeutic measures can be taken. In the recovery room and the further care station the patient can also be correspondingly treated or further progress can be monitored carefully.

The second aspect of the invention can be implemented independently of the first aspect of the invention or in combination therewith.

One embodiment of the second aspect of the invention provides that the predefined amount, below which an increase in the power of the alpha band from the first power to the second power must lie in order for the information to be provided, is determined in that for a plurality of patients that have not developed postoperative delirium, the average first power of the alpha band is compared with the average second power of the alpha band, a first reference value being created, for a plurality of patients that have developed postoperative delirium, the average first power of the alpha band is compared with the average second power of the alpha band, a second reference value being created, and the predefined amount is created on the basis of the difference or on a relationship between the first reference value and the second reference value.

The evaluation of the difference in the power of the alpha band of a patient under observation between the preoperative and intraoperative state as to whether a condition is present in which the likelihood of postoperative delirium occurring is greater, is therefore carried out on the basis of reference values, on the basis of which the "predefined amount" relevant in this respect is formed. The reference values are established in patients that have or have not developed postoperative delirium.

In this case, the comparison of the average first power of the alpha band with the average second power of the alpha band in order to form the first and second reference value can be carried out by creating the difference or quotient of these values, for example.

One embodiment provides that the predefined amount is created by the difference between the first reference value and the second reference value plus a percentage or absolute tolerance value. In this case, the percentage tolerance value can correspond to the standard deviation, for example.

Another embodiment provides that the predefined amount is determined on the basis of the age bracket of the patient. For example, for both groups, reference values are established for a first age bracket (for example 65-70 years) and reference values are established for a second age bracket (for example 70-80 years). For a patient under observation, the reference values for their age bracket are used to improve the likelihood of correctly predicting that postoperative delirium has occurred.

Another embodiment provides that the first power of the alpha band and the second power of the alpha band and the increase in the power of the alpha band from the first power to the second power is determined in dB, and that the amount, below which an increase in the power of the alpha band from the first power to the second power must lie in order for the information to be provided and checked, is likewise given in dB. Corresponding power values in dB are directly output by modern EEG anesthesia monitors and can therefore be obtained in a simple manner.

One embodiment provides that the increase in the power of the alpha band from the first power to the second power has to be below 15 dB, in particular below 12 dB, in order for the information to be provided or the parameter generated.

In the second aspect of the invention, too, according to one embodiment the power of the alpha band is determined on an EEG signal after this has been filtered through a band-pass filter. At least one frontal EEG signal is preferably recorded on the patient's head, whereby a plurality of frontal EEG signals from the patient can be recorded that are averaged in order to determine the power of the alpha band. For example, the signal is deduced at electrodes positioned in positions F7, F8, Fp1, Fp2 and Fpz in the 10-20 system.

In a third aspect, the invention provides a method for providing another parameter that indicates a heightened likelihood of postoperative delirium occurring. According to the method, at least one EEG signal is recorded on the patient's head, whereby only the frequency range of the EEG signal that is below 0.5 Hz is recorded or taken into consideration. Signals in this frequency range are also referred to as "direct current EEG" or "DC-EEG" since the change in the signal is very slow. According to one embodiment, in this case all the signals having a frequency of less than 0.5 Hz are recorded. In an alternative embodiment, the frequency range under consideration can be further restricted, for example to signals having a frequency of less than 0.1 Hz.

According to the method in the third aspect of the invention, the average amplitude of the EEG signal is determined in a current timeframe of the EEG signal. The timeframe under consideration takes into account the EEG signal in a period that spans a defined period from the current point in time, for example an EEG signal over the period of two minutes or one minute or over the last 30, 20, 10 or 2 seconds. In this respect, this is a timeframe that migrates over time or the determination of an amplitude measurement over time. The average amplitude can be determined continuously or in specific intervals.

The curve of the average amplitude of the EEG signal between a preoperative point in time before an anesthesia-inducing medication is administered and an intraoperative point in time after entering the anesthetic-induced loss of consciousness is determined. In this case, in particular the average amplitude of the EEG signal is determined when entering the anesthetic-induced loss of consciousness. Entering the loss of consciousness ("LOC") under anesthesia can be accurately recorded by means of the blink reflex, for example.

Furthermore, a check is made to see whether an increase in the average amplitude of the EEG signal when entering the anesthetic-induced loss of consciousness is above a predefined amount. If so, a corresponding piece of information is provided or output as a parameter that indicates a heightened likelihood of postoperative delirium occurring.

Subsequently, i.e., after entering the anesthetic-induced loss of consciousness, the average amplitude drops again such that the average amplitude of the EEG signal when entering the anesthetic-induced loss of consciousness comprises a peak and can be accordingly easily recorded using measurements.

This third aspect of the invention relates to the surprising knowledge that patients in whom the average amplitude of the "direct current" EEG signal (i.e., of the signal component of the EEG signal having a frequency of less than 0.5 Hz) experiences a significant increase at the point in time when consciousness is lost, together with a significantly greater likelihood of developing postoperative delirium. In patients that do not develop postoperative delirium, by contrast there is no increase, or no significant increase, in the average amplitude of the "direct current" EEG signal when consciousness is lost.

The third aspect of the invention can be implemented independently of the first and second aspects of the invention or in combination with one or both thereof.

In order to record the "direct current" EEG signal, the EEG signal may pass through a low-pass filter having a cutoff frequency of 0.5 Hz.

According to one embodiment of the third aspect of the invention, the predefined amount, above which an increase in the average amplitude of the EEG signal has to lie when entering the anesthetic-induced loss of consciousness in order for information to be provided, is determined by the average amplitude of the EEG signal when entering the anesthetic-induced loss of consciousness being determined for a plurality of patients that have not developed postoperative delirium, wherein a first reference value is created. Furthermore, for a plurality of patients that have developed postoperative delirium, the average amplitude of the EEG signal when entering the anesthetic-induced loss of consciousness is determined, wherein a second reference value is created. The predefined amount is created on the basis of the difference or a relationship between the first reference value and the second reference value. For example, the second reference value can be greater than the first reference value at least by a factor of 3, in particular at least by a factor of 5, in particular at least by a factor of 10, in order for the predetermined amount to be exceeded.

In this case, the predefined amount can be formed by the difference between the first reference value and the second reference value minus a percentage or absolute tolerance value. Furthermore, the predefined extent can be determined on the basis of the age bracket of the patient.

In the third aspect of the invention, according to one variant of the invention, the EEG signal is deduced at an electrode positioned in position Cz (i.e., centrally) in the 10-20 system, and at a reference electrode, for example on the ear. For this central EEG deduction, the best signals were experimentally recorded. Alternatively, however, the deduction can also take place frontally, again via electrodes positioned in positions F7, F8, Fp1, Fp2 and Fpz, for example.

The methods according to the invention are automated, in particular carried out by a computer program. For example, a computer program contains a program code for carrying out the method according to claim 1 and/or a program code for carrying out the method according to claim 11 and/or a program code for carrying out the method according to claim 20 when the computer program is executed on a computer.

In another aspect of the invention, the invention relates to a device for providing a parameter that indicates a heightened likelihood of postoperative delirium occurring, wherein the device comprises:
  means for recording at least one EEG signal on the patient's head,
  means for determining the intraoperative alpha peak frequency of the EEG signal, wherein the alpha peak frequency in the power spectrum of the EEG signal is the frequency in the alpha band at which the power is greatest,
  means for checking whether the intraoperative alpha peak frequency determined is significantly lower than a preset reference value for the alpha peak frequency, and
  means for providing a corresponding piece of information as a parameter indicating a heightened likelihood of postoperative delirium occurring.

In another aspect of the invention, the invention relates to a device for providing a parameter indicating a heightened likelihood of postoperative delirium occurring, wherein the device comprises:
  means for recording at least one EEG signal on the patient's head,
  means for determining the power of the alpha band of the EEG signal, wherein the power of the alpha band in the power spectrum of the EEG signal is defined as the integral of the power across all the frequencies in the alpha band,
  wherein a first power of the alpha band is determined at a preoperative point in time before an anesthesia-inducing medication is administered, and a second power of the alpha band is determined at an intraoperative point in time after entering the anesthetic-induced loss of consciousness,
  means for checking whether an increase in the power of the alpha band from the first power to the second power is below a predefined amount, and
  means for providing a corresponding piece of information as a parameter that indicates a heightened likelihood of postoperative delirium occurring.

In another aspect of the invention, the invention relates to a device for providing a parameter that indicates a heightened likelihood of postoperative delirium occurring, wherein the device comprises:
  means provided and designed to record at least one EEG signal on the patient's head, wherein only the frequency range of the EEG signal that is below 0.5 Hz is recorded or taken into consideration,
  means provided and designed to determine the average amplitude of the EEG signal in a current timeframe of the EEG signal,
  means provided and designed to determine the curve of the average amplitude of the EEG signal between a preoperative point in time before an anesthesia-inducing medication is administered, and an intraoperative point in time after entering the anesthetic-induced loss of consciousness,
  wherein the average amplitude of the EEG signal is determined when entering the anesthetic-induced loss of consciousness,
  means provided and designed to check whether an increase in the average amplitude of the EEG signal of the anesthetic-induced loss of consciousness is above a preset amount, and
  if so, means provided and designed to provide a corresponding piece of information as a parameter indicating a heightened likelihood of postoperative delirium occurring.

Said means can be formed by a microprocessor in conjunction with a program code that the microprocessor executes. Said parameter is displayed on a monitor, for example.

Furthermore, the devices are designed and set up to carry out the method steps indicated in claims 2-10, 11-18 and 20-25 and comprise corresponding means therefor.

In another aspect, the invention relates to an EEG anesthesia monitor comprising a device according to claim 26 and/or comprising a device according to claim 35 and/or comprising a device according to claim 44. The device according to the invention is therefore integrated in an EEG anesthesia monitor, wherein this is provided and designed to analyze EEG data in real time.

The invention will be explained in more detail in the following with reference to the figures in the drawings and on the basis of several embodiments, in which.

Figure 4:
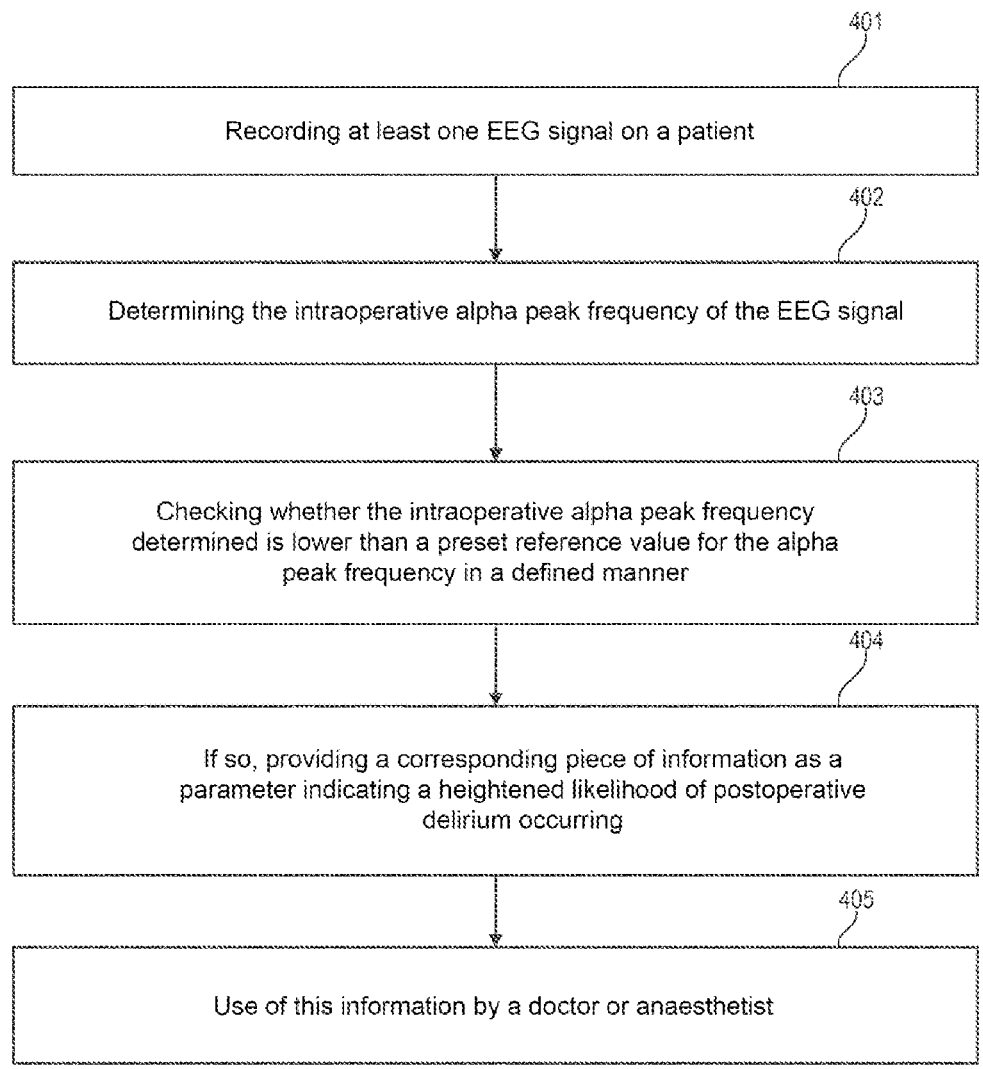
FIG. 4 is a flow diagram of a first method for providing a parameter indicating a heightened likelihood of postoperative delirium occurring.
Figure 5:
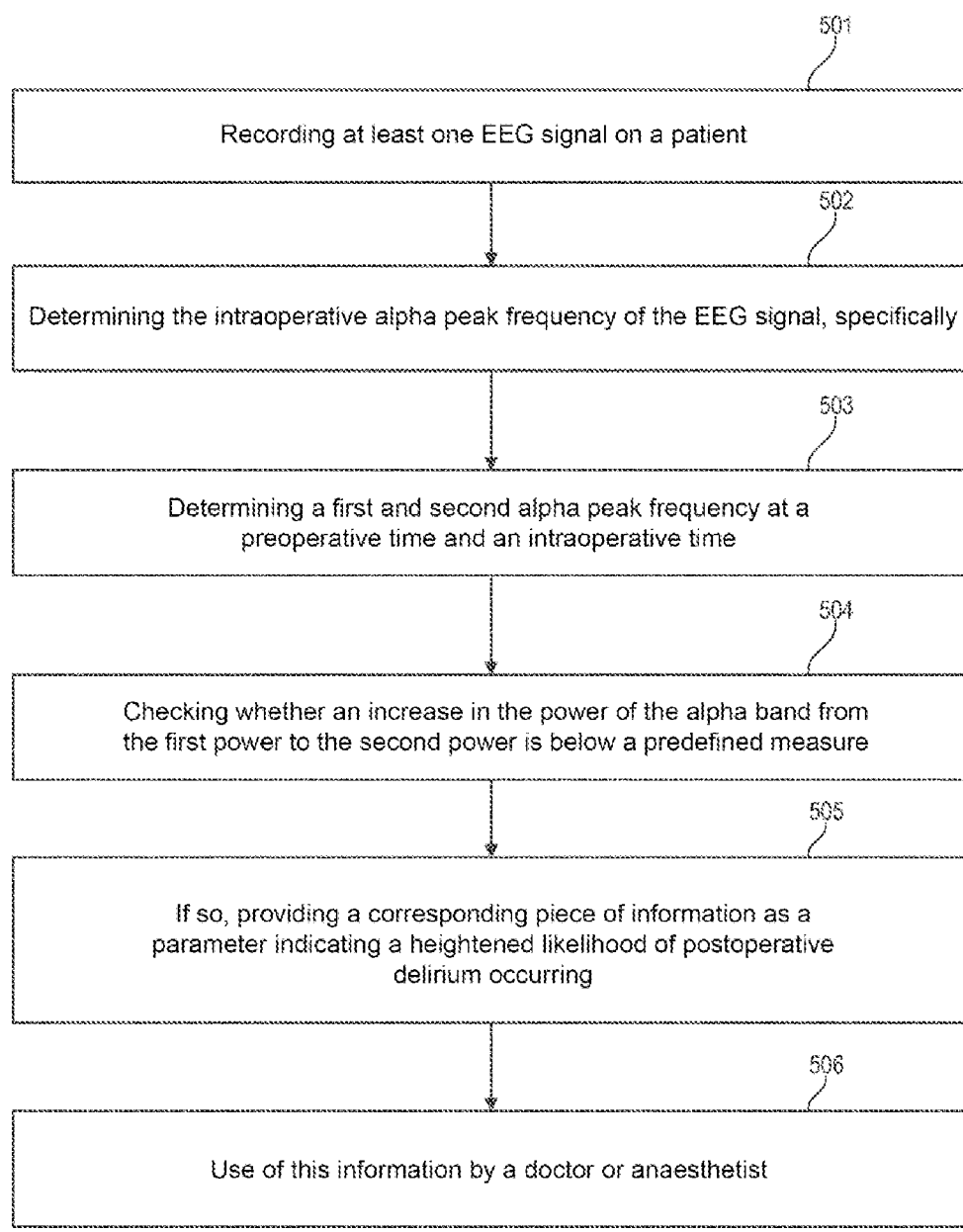
FIG. 5 is a flow diagram of a second method for providing a parameter indicating a heightened likelihood of postoperative delirium occurring.
Figure 6:
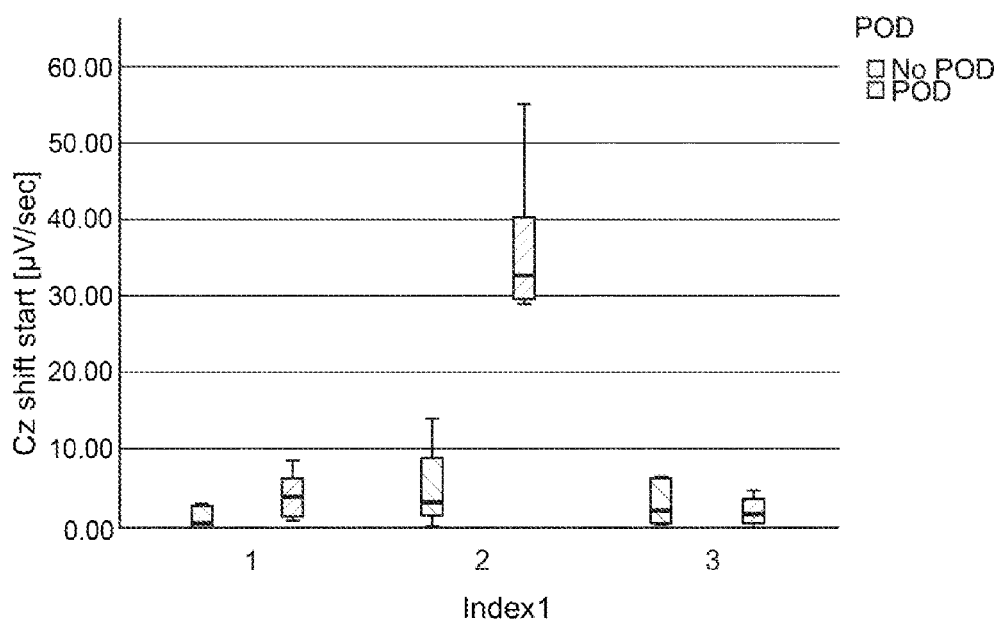
Figure 7:
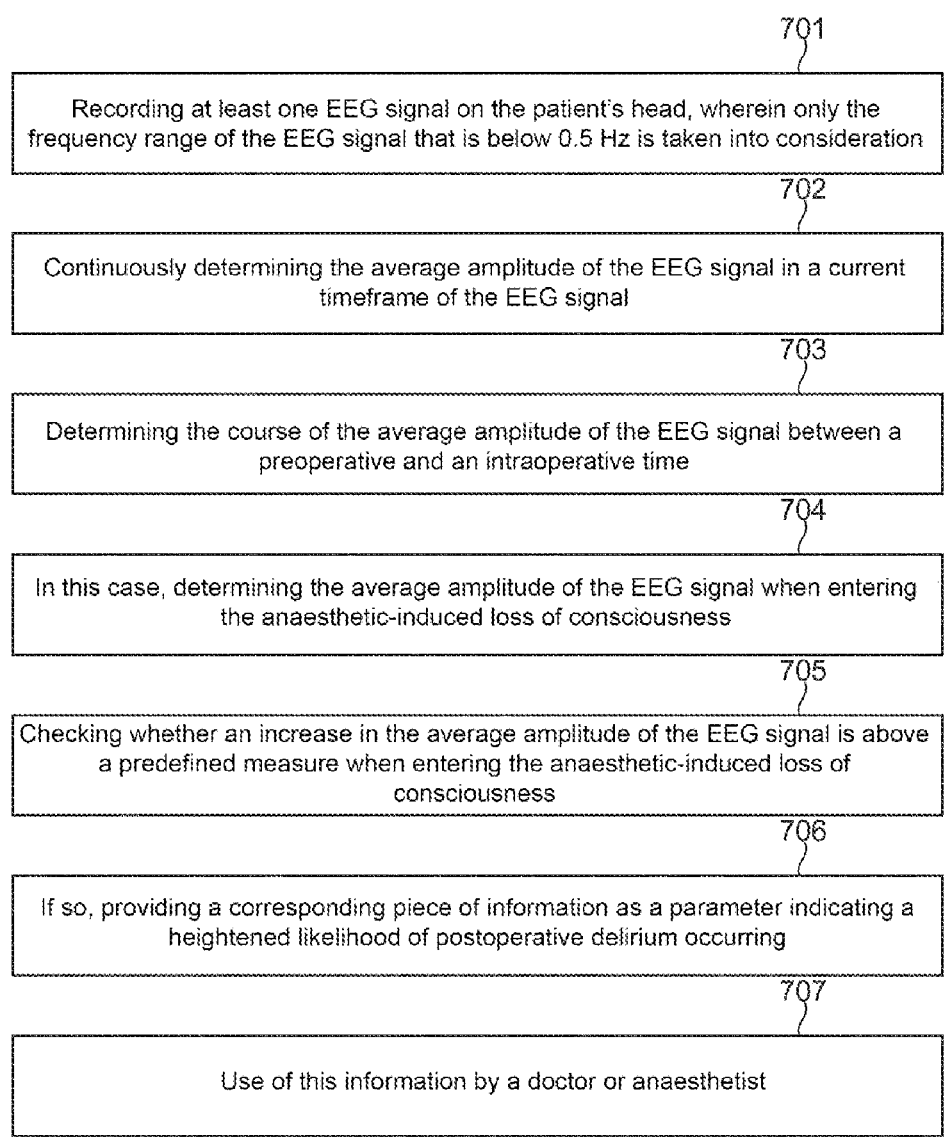
Figure 8:
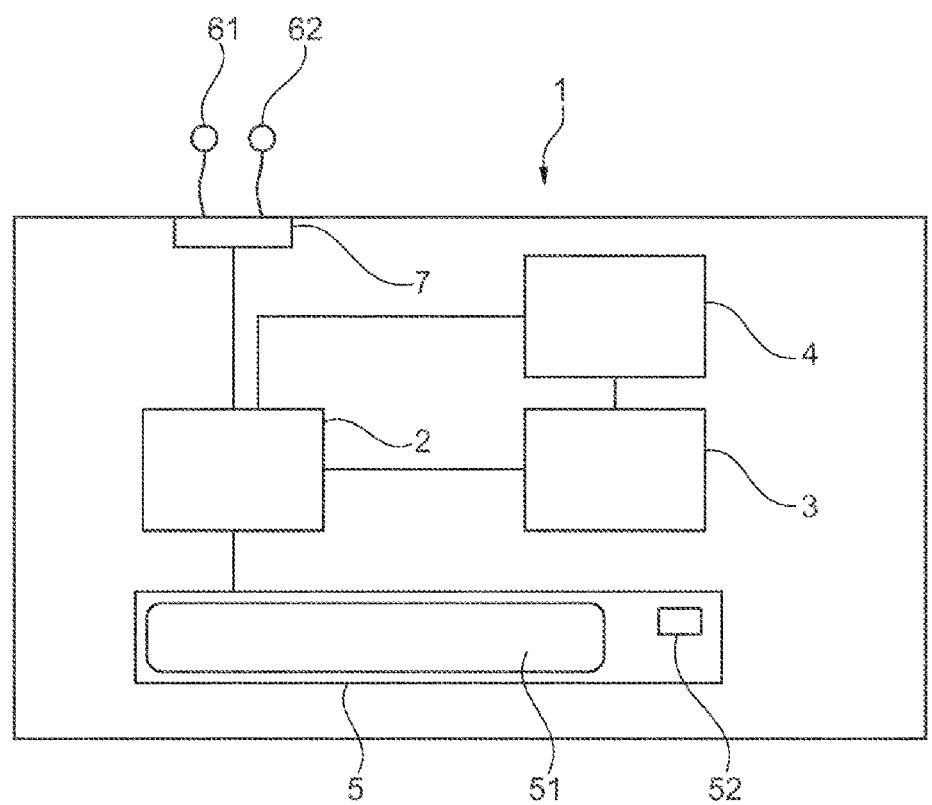
Figure 9:
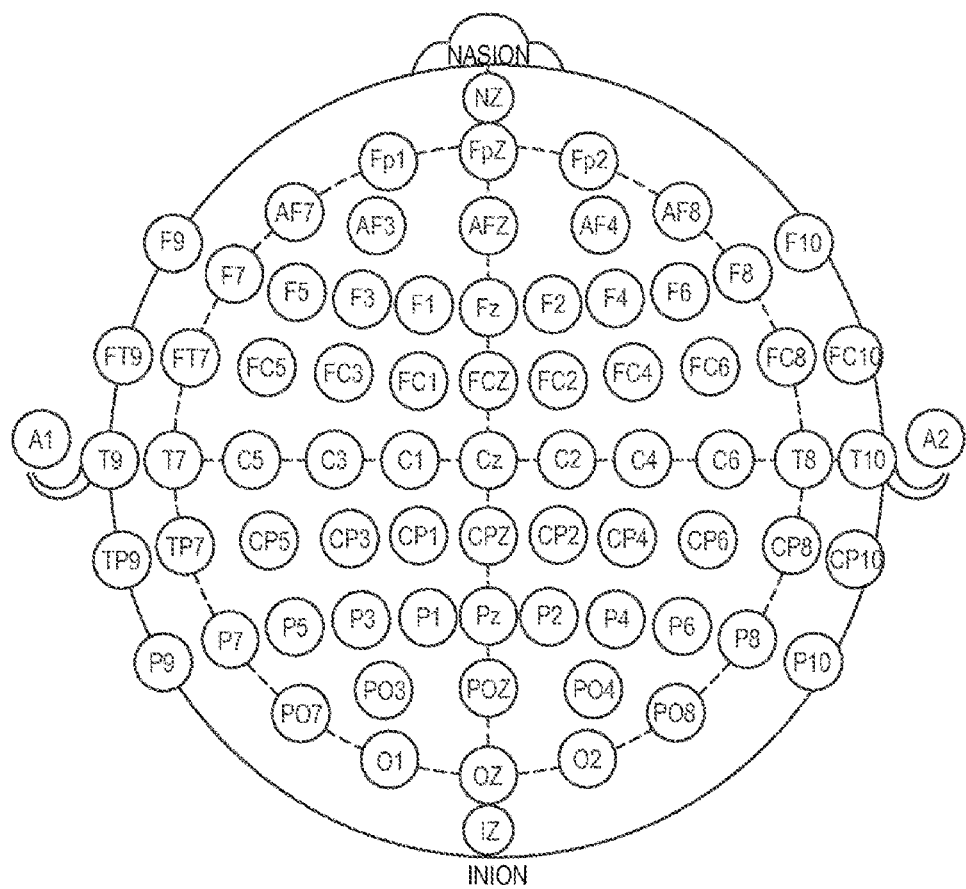

FIG. 6 shows, by way of example, the average amplitude of the direct current EEG signal at a time point (1) before an anesthetic is introduced, at the time point (2) when consciousness is lost and at a time point (3) after consciousness has been lost, wherein the average amplitude for a patient group that has developed postoperative delirium (POD) significantly increases at the point in time at which consciousness is lost;

FIG. 7 is a flow diagram of a third method for providing a parameter indicating a heightened likelihood of postoperative delirium occurring;

FIG. 8 shows, by way of example, a device for carrying out the methods in FIG. 4 and/or FIG. 5 and/or FIG. 7; and FIG. 9 shows positioning points for EEG electrodes according to the 10-20 system.

The invention comprises three variants of the invention, wherein one variant of the invention looks at the determination of the intraoperative alpha peak frequency of a patient, the second variant of the invention looks at the determination of the difference between the preoperative and the intraoperative power of the alpha band of a patient, and the third variant of the invention looks at the determination of the average amplitude of the "direct current" EEG signal and the curve thereof when entering the anesthetic-induced loss of consciousness.

The relationship recognized for the first time according to the first variant of the invention will be explained on the basis of FIGS. 1 and 2, which relationship has been proven by means of a study. The relationship recognized for the first time according to the second variant of the invention will be explained on the basis of FIGS. 1 and 3, which relationship has been proven by means of a study. The relationship recognized for the first time according to the third variant of the invention will be explained on the basis of FIG. 6, which relationship has been proven by means of a study.

Figure 1:
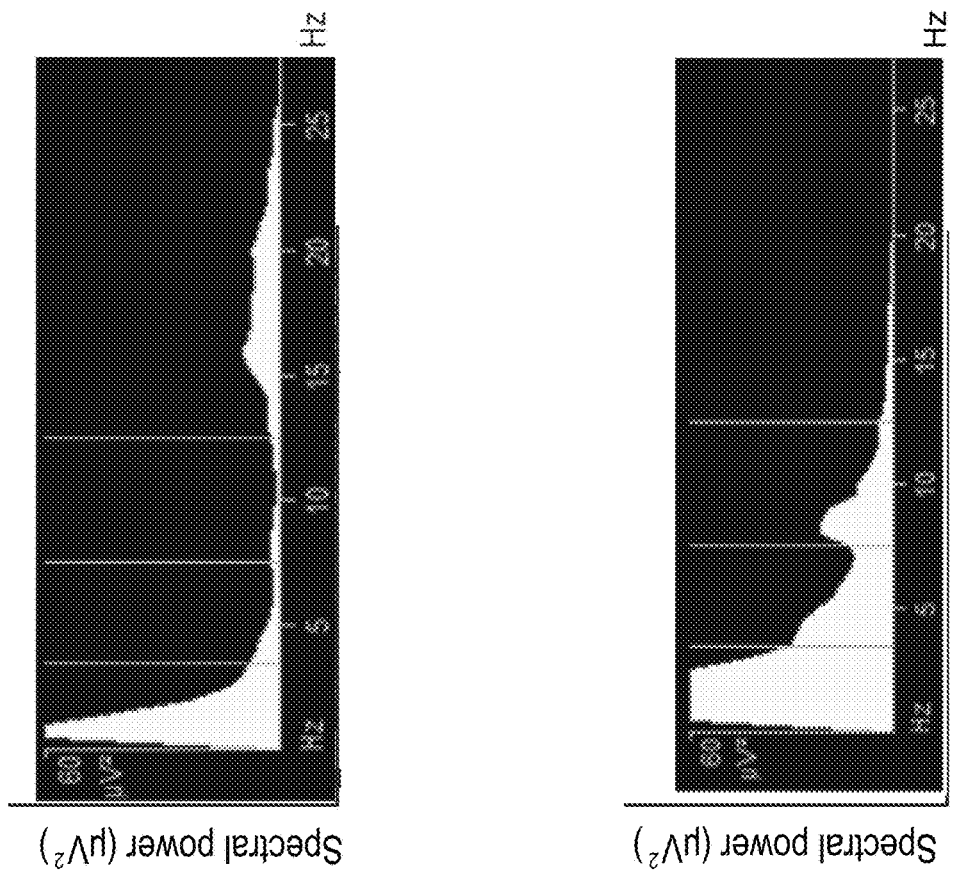
FIG. 1 shows, by way of example, EEG signals in the awake state and after an anesthetic-induced loss of consciousness both as a time-dependent signal and in the power spectrum in each case.
Figure 1:
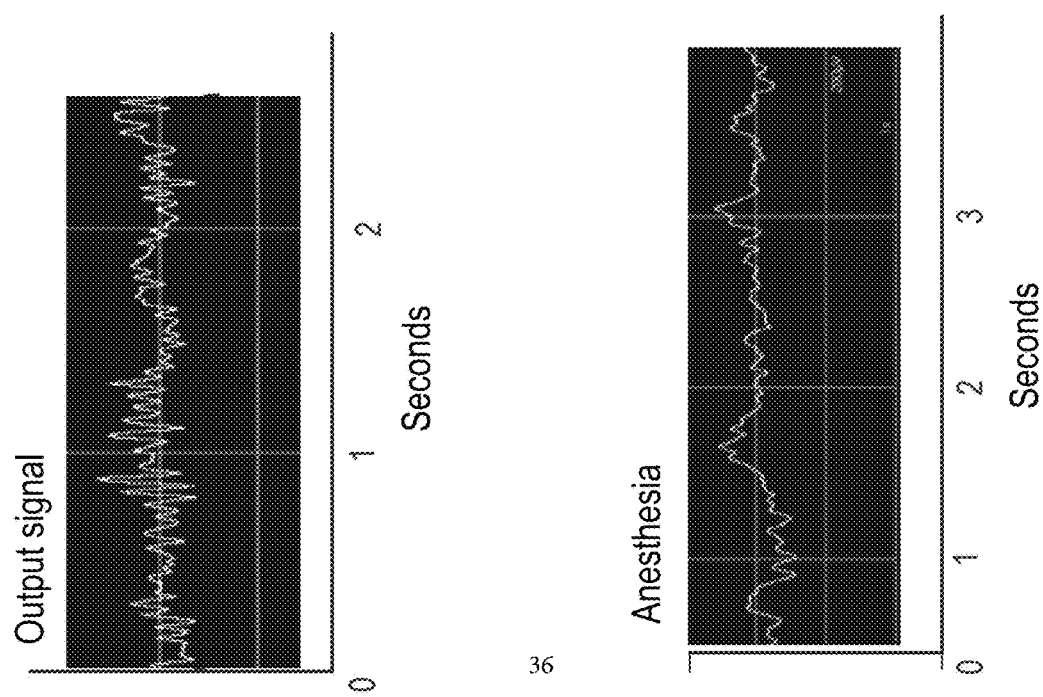

In order to explain the background of the invention, FIG. 1 shows in the upper representation ("Baseline") an EEG signal as occurs in a patient who is awake. The signal is both depicted as a time signal (left) and as a power spectrum (right) after a spectral analysis. In the power spectrum, the power (square amplitude) is plotted in $\mu V^2$ against the frequency in Hz. The power spectrum reflects the respective proportions of the individual frequency ranges in the overall power proportion of the raw signal.

The bottom representation ("anesthesia") in FIG. 1 shows an EEG signal under anesthesia. It is clear that the frequency spectrum as a whole is shifted to the left with respect to the value in a patient who is awake. In detail, the frequencies increase under anesthetic from the delta, theta, and alpha band, whilst the beta and gamma waves decrease. In this case, Purdon P L, Pierce E T, Mukamel E A, Prerau M J, Walsh J L, Wong K F K, Salazar-Gomez A F, Harrell P G, Sampson A L, Cimenser A, Ching S, Kopell N J, Tavares-SToeckel C, Habeeb K, Merhar R, Brown E.: "Electroencephalogram signatures of loss and recovery of consciousness from propofol," PNAS 2013; 110 (12): E1142-1151, have shown that a characteristic frontal alpha band activation occurs first and foremost in the event of deep unconsciousness induced by GABA-activating anesthetic.

Figure 2:
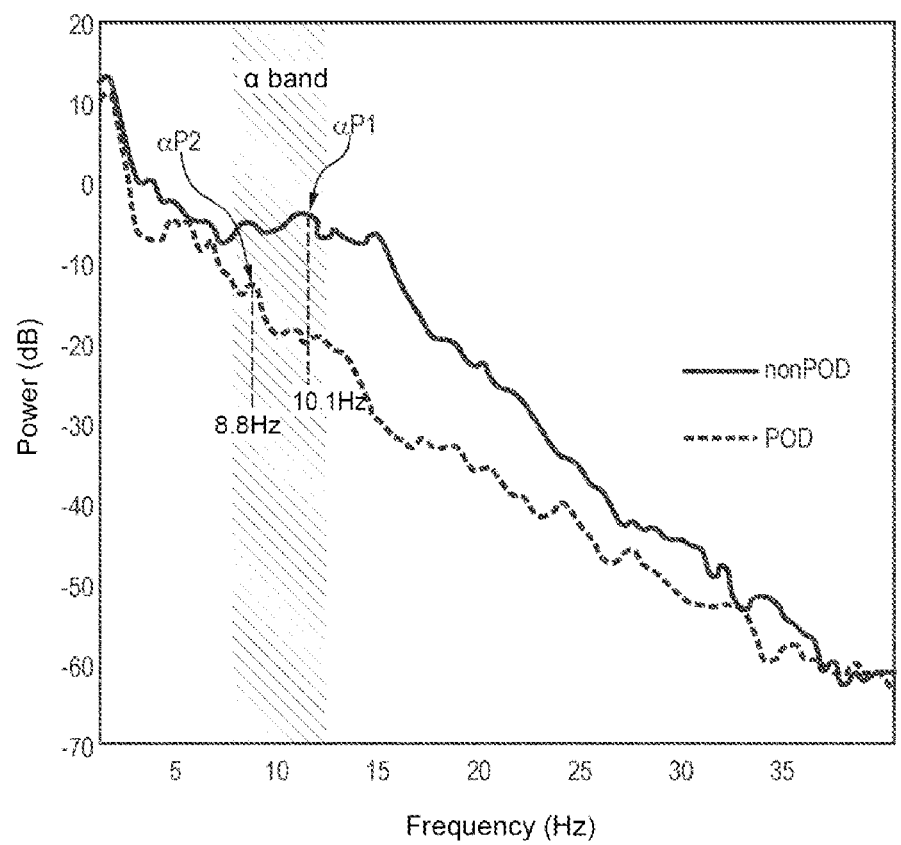
FIG. 2 shows, by way of example, the intraoperative alpha peak in the power spectrum frequency for both a patient group that has not developed postoperative delirium (non-POD) and for a patient group that has developed postoperative delirium (POD)

FIG. 2 shows the intraoperative alpha peak frequency for both a patient group that has not developed postoperative delirium and for a patient group that has developed postoperative delirium in the power spectrum in which the power is plotted in dB against the frequency. The alpha peak frequency is defined in this case as the frequency in the alpha band at which the power is greatest. Alternatively, the theta band or the upper part of the theta band (between 6 and 8 Hz) can additionally be taken into consideration, i.e., the alpha peak frequency is defined as the frequency in the alpha band and theta band (or upper region of the theta band) at which the power is greatest.

In this case, in a prospective observation study of the relationship, it was possible to show that the intraoperative alpha peak frequency in patients that do not develop postoperative delirium after the operation (non-POD) is greater than in patients that develop postoperative delirium after the operation (POD). Therefore, the alpha peak frequency $\alpha_{p1}$ for non-POD patients is 10.1 hertz in the figure. In POD patients, the alpha peak frequency $\alpha_{p2}$ is 8.8 hertz, and therefore significantly lower. The standard deviation of the value from 10.1 hertz was 0.77 hertz. The standard deviation of the value from 8.8 hertz was 0.87 hertz.

The study was carried out on an age-matched patient group having 11 POD patients and 11 non-POD patients. It was therefore possible to show that the intraoperative alpha peak frequency in POD patients is significantly lower than in non-POD patients.

Figure 3:
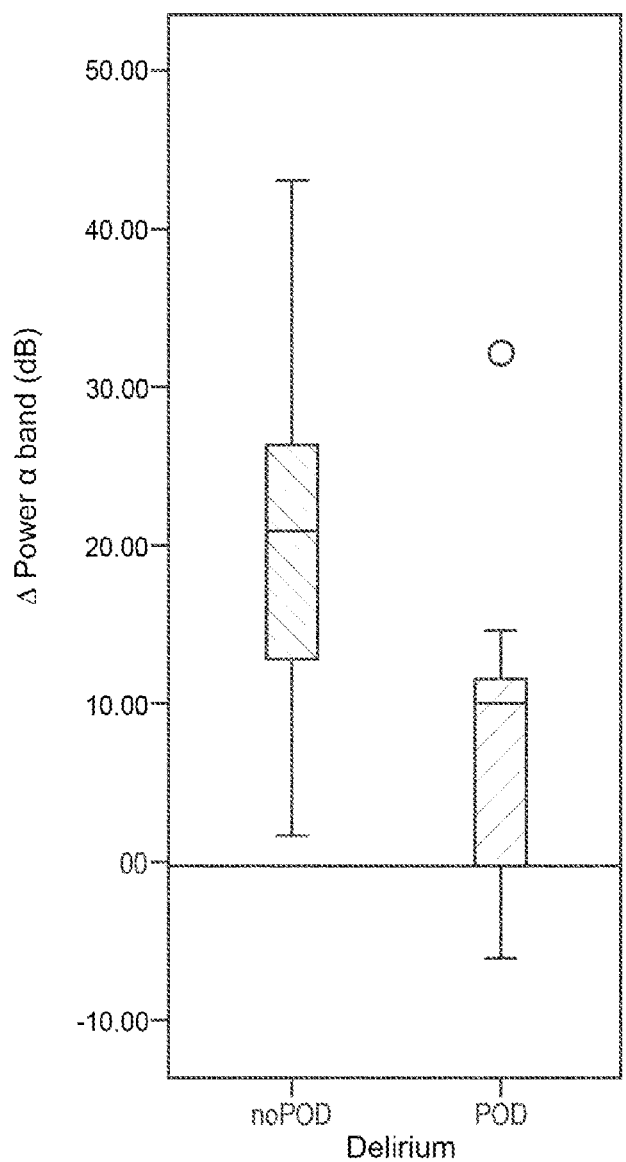
FIG. 3 shows, by way of example, the difference between the preoperative and the intraoperative power of the alpha band measured in dB, wherein the powers of the alpha band were measured for both a patient group that has not developed postoperative delirium (nonPOD) and for a patient group that has developed postoperative delirium (POD)

FIG. 3 shows the difference between the preoperative and the intraoperative power of the alpha band measured in dB for a non-POD patient group and for a POD patient group in a diagram. In this case, the relationship whereby the power of the alpha band from preoperative to intraoperative increased less strongly in POD patients than in non-POD patients could be shown in a prospective observation study. Therefore, according to FIG. 3 the average of the difference Δ from intraoperative to preoperative for non-POD patients is approximately 21 dB. In POD patients, this average is approximately 10 dB, and is therefore significantly lower. The standard deviation in non-POD patients was approximately 13 dB. The standard deviation in POD patients was approximately 11.5 dB. The standard deviation is likewise shown in FIG. 3.

The study was carried out on a patient group having 19 POD patients and 35 non-POD patients over 65 years old, wherein anesthesia was initiated using one of the most commonly used anesthetics, specifically propofol. It was therefore possible to show that the increase in the power of the EEG signal in the alpha band from preoperative to intraoperative in POD patients significantly reduced and the difference in the power in the alpha band from intraoperative to preoperative was accordingly significantly smaller in POD patients.

The measurements according to FIGS. 2 and 3 were made as follows:

a) Eeg Deduction:

A continuous intraoperative EEG was recorded using an EEG-based brain function monitor (the "SED-Line Monitor" by Masimo Corporation, Irvine, California) from the beginning of the anesthesia to the end of the anesthesia. The surfaces of EEG the self-adhesive electrodes (by Masimo, 4248RDSEDLine sensor, Single Patient Use, Non-Sterile) were applied in positions F7, F8, FP1 and FP2 according to the 10/20 system, with Fpz as a ground electrode and the reference approximately 1 cm above Fpz; cf. FIG. 8. For this, the forehead and the temples of the patient were thoroughly disinfected and rid of skin oils. The impendence of the individual electrodes was below 5 kΩ, the sampling frequency was 250 Hz.

After connecting the self-adhesive electrodes to the EEG-based brain function monitor, the deduction and recording of a continuous 4-channel EEG was begun. The patients were still awake at this point such that the first values for the deduction corresponded to a baseline activity. In order to determine defined points in time during the EEG deduction, "event markers" were manually placed in the EEG during the EEG recording. Event marker: "baseline"=awake patient, before anesthetic is administered, "start anesthesia"=begin anesthetic administration, "loss of consciousness"=lack of blink reflex, "ITN"=intubation of the patient, "OP"=stable intraoperative phase 15-30 min after ITN. All patients were given the medication propofol intravenously in order to initiate the anesthesia, anesthesia was maintained using IV propofol or using the inhalation anesthetic desflurane or sevoflurane. The EEG data recorded were exported from the SEDLine monitor.

b) Eeg Evaluation:

The raw EEG data were provided by a band-pass filter of 0.5-40 Hz (Brain Vision Analyzer Software). A visual EEG data analysis was then carried out, wherein at each of the time points "Baseline" and "OP" a 10-second artifact-free EEG timeframe was selected. The EEG data were segmented into a "Baseline" and an "Intraoperative" EEG. The further data analysis was carried out by means of the Chronux Toolbox (Bookil et al, 2010) for Matlab (The MathWorks, Inc., Natick, Massachusetts, United States). The power spectrum over all the frequency bands (slow and fast delta, theta, alpha, beta) was calculated by means of Multitaper methods with 2 second timeframes, with 1.9 seconds of overlapping, time bandwidth product TW=3, number of tapers K=5 and spectral resolution of 2 W=3 Hz. The calculation was carried out by means of digital computer-assisted EEG signal processing. The basis for this is the spectral analysis of the raw EEG by means of Fast Fourier Transform, by means of which power proportions can be calculated for the timeframe to be currently analyzed in each case.

The data were then transformed into a decibel scale [Power(dB)=10 log 10(Power(μV))]. In order to be able to image the frontal EEG power more effectively, a pooled frontal electrode was calculated, into which the equally weighted signals from the electrodes Fp1, Fp2, F7 and F8 flowed.

By means of the spectra determined, the peak frequency (Hz) in the alpha band (8-12 Hz) (aPF) was determined according to FIG. 2. Furthermore, the difference between the power of the signal in the alpha band between intraoperative and preoperative was calculated according to FIG. 3 (difference between alpha band power OP and alpha band power baseline).

c) Delirium Screening:

After the operation, the routine creation of a delirium scoring was carried out after admission into the recovery room. The postoperative delirium was defined on the basis of the DSM V (Diagnostic and Statistical Manual of Mental Disorders) criteria. During the stay in the recovery room, the nurse detection score (NuDESC) was created at regular intervals. All patients with an NuDESC score of 2 at any point during the stay in the recovery room are characterized as patients having postoperative delirium (POD group), patients having an NuDESC score of 1 are characterized as patients not having postoperative delirium (NonPOD group).

d) Statistical Evaluation:

Statistical calculations for the alpha peak frequency and the difference between the alpha band power OP and the alpha band power baseline were made using SPSS, version 24 (Copyright SPSS, Inc., Chicago, IL 60606, USA) by means of Mann-Whitney U tests and Kruskal-Wallis test.

According to the invention, the relationships established are evaluated electronically or in a computer-based manner and used to determine the intraoperative alpha peak frequency or the size of the increase in the power of the EEG signal in the alpha band from preoperative to intraoperative in a patient. The associated program can be integrated in an EEG-based brain function monitor or electroencephalograph as a software tool in this case.

FIG. 4 shows a first method for determining a parameter that indicates a heightened likelihood of postoperative delirium occurring. According to step 401, at least one frontal EEG signal from a patient is recorded. For example, four EEG signals are picked up by means of electrodes in positions F7, F8, FP1 and FP2 according to the 10/20 system, with Pfz as the reference electrode, and these signals are averaged. An additional ground electrode is placed just above Fpz.

According to step 402, the intraoperative alpha peak frequency of the EEG signal is then determined. This is performed at a point in time when the patient is in a stable state of anesthesia, for example 15-30 minutes after consciousness has been lost. Next, a check is made to see whether the intraoperative alpha peak frequency measured is significantly lower than a predetermined reference value for the alpha peak frequency. In this case, the preset reference value was established beforehand by averaging the intraoperative alpha peak frequencies measured for a plurality of patients that did not develop postoperative delirium. In this case, the preset reference value is selected so as to be adapted to the age bracket of the patient. In this case, the currently determined intraoperative alpha peak frequency is, for example, then significantly lower with respect to the preset reference value when the difference between the preset reference value and the intraoperative alpha peak frequency measured exceeds a defined percentage deviation from the reference value or a defined absolute difference between the intraoperative alpha peak frequency and the reference value. According to the values in FIG. 2, the reference value is 10.1 hertz and a significant deviation is assumed, for example, if the alpha peak frequency value measured is below 9.5 hertz.

In this case, according to step 404 a corresponding piece of information is provided as a parameter, which indicates a heightened likelihood of postoperative delirium occurring.

FIG. 5 shows a second method for determining a parameter that indicates a heightened likelihood of postoperative delirium occurring. According to step 501, once again at least one frontal EEG signal is recorded on a patient. For example, four EEG signals are picked up by means of electrodes in positions F7, F8, FP1 and FP2 according to the 10/20 system, with Fpz as the reference electrode, and an average is taken of these signals.

According to step 502, the power of the alpha band of the EEG signal is then determined, wherein the power of the alpha band in the power spectrum of the EEG signal is defined as the integral of the power over all the frequencies in the alpha band. Therefore, according to step 503, a first power of the alpha band is determined at a preoperative point in time that is before an anesthetic-inducing medication is administered, and a second power of the alpha band is determined at an intraoperative point in time after entering the anesthetic-induced loss of consciousness.

A check is then made to see whether an increase in the power of the alpha band from the first power to the second power is below a predefined amount. The predefined amount has, for example, been established using reference values that were measured in POD patients and nonPOD patients. The predefined amount can, for example, be a specific dB value that is the maximum by which the power of the alpha band can increase from preoperative to intraoperative so that there is a significant difference. According to the values in FIG. 3, the preset amount is 15 dB, for example, i.e., when the power in the alpha band increases from preoperative to intraoperative by less than 15 dB, a significance is assumed. In such a case, according to step 505 a corresponding piece of information is provided as a parameter that indicates that postoperative delirium has occurred.

FIG. 6 shows measured values for the third variant of the invention, which takes into consideration the determination of the average amplitude of the "direct current" EEG signal and the curve thereof when entering the anesthetic-induced loss of consciousness. In this context, reference is first made to the fact that commercially available EEG-based brain function monitors have a high-pass filter that filters out the frequency range of the signal that is below 0.5 Hz. The third variant of the invention differs from this and in particular recognizes the frequency range below 0.5 Hz, which is also referred to as the "direct current" EEG or DC-EEG. For this purpose, the measured signal can pass through a low-pass filter with a cutoff frequency of 0.5 Hz, for example.

The measured DC-EEG signal is continuously evaluated with regard to its amplitude, the average amplitude being calculated in a current concurrent timeframe. This average amplitude is to be distinguished from the signal average, from which the amplitude is measured. The signal average is, for example, established in the same timeframe or over a longer timeframe or over the entire measuring time or defined by the EEG-based brain function monitor.

FIG. 6 shows the measurement of the average amplitude at three time points 1, 2, 3, wherein time point 1 is a preoperative time point before an anesthetic-inducing medication is administered, time point 2 characterizes the entrance of the anesthetic-induced loss of consciousness and time point 3 is a point in time after entering the anesthetic-induced loss of consciousness. The average amplitude is plotted on the y-axis, which is labeled as the "Cz shift," since the deduction took place at point Cz in the 10-20 system (cf. FIG. 9), wherein this is only to be understood by way of example.

Furthermore, FIG. 6 differentiates between POD patients and nonPOD patients.

At time point 1, the average amplitude of the DC-EEG signal is relatively low both for POD patients and for nonPOD patients. The values for a group statistic at time point 1 for a patient group where N=7 POD patients and N=9 nonPOD patients are indicated in the following.

| Group statistics | | | | | |
|---|---|---|---|---|---|
| | POD | N | average | Std. deviation | Standard error of the average |
| Cz shift start [µV/sec] | No POD | 9 | 6.1808 | 11.33645 | 3.77882 |
| | POD | 7 | 3.9513 | 3.25966 | 1.23204 |

At time point 2, i.e., when entering the anesthetic-induced loss of consciousness, the average amplitude increased significantly in the POD patients, while it only increased slightly in the nonPOD patients. The values for a group statistic at time point 2 for a patient group where N=7 POD patients and N=7 nonPOD patients are indicated in the following.

| Group statistics | | | | | |
|---|---|---|---|---|---|
| | POD | N | average | Std. deviation | Standard error of the average |
| Cz shift LOC [µV/sec] | No POD | 7 | 5.5001 | 5.60270 | 2.11762 |
| | POD | 7 | 33.1340 | 16.15877 | 6.10744 |

The significance of the increase in the average amplitude from time point 1 to time point 2 for the POD patients is 0.003 (Kruskal-Wallis test), i.e., there is a clear significance.

At time point 3, i.e., at an intraoperative point in time after entering the anesthetic-induced loss of consciousness, the average amplitude both in the POD patients and in the nonPOD patients dropped again. There was therefore only a peak in the curve in the POD patients. The values for a group statistic at time point 3 for a patient group where N=7 POD patients and N=10 nonPOD patients are indicated in the following.

| Group statistics | | | | | |
|---|---|---|---|---|---|
| | POD | N | average | Std. deviation | Standard error of the average |
| Cz shift intraOP [µV/sec] | No POD | 10 | 5.1154 | 6.11759 | 1.93455 |
| | POD | 7 | 4.4911 | 7.11296 | 2.68844 |

The DC-EEG signal was measured during the measurements, as explained. The electrode position Cz was used for the deduction (cf. FIG. 9). However, the same dynamic was shown across the entire cortex such that a frontal or high frontal deduction can also take place.

FIG. 7 shows, by way of example, the associated method for determining a parameter that indicates a heightened likelihood of postoperative delirium occurring. According to step 701, at least one EEG signal is recorded on the patient's head, wherein only the frequency range of the EEG signal that is below 0.5 Hz is taken into consideration, i.e., the direct current EEG signal or DC-EEG signal. For example, a deduction is carried out by means of an electrode in position Cz and a reference electrode on the ear, for example.

According to step 702, the average amplitude of the EEG signal is continuously determined in a current timeframe of the EEGs signal. This continuous determination of the average amplitude allows for the determination of the curve of the average amplitude of the EEG signal between a preoperative and an intraoperative point in time according to step 703. In this case, in step 704 the average amplitude of the EEG signal is determined when entering the anesthetic-induced loss of consciousness.

In step 705, a check is made to see whether an increase in the average amplitude of the EEG signal when entering the anesthetic-induced loss of consciousness has taken place and, if so, whether the increase is above a predefined amount. In this case, the predefined amount is established by means of two reference values, for example, wherein the first reference value indicates the average amplitude of the EEG signal when entering the anesthetic-induced loss of consciousness in a plurality of nonPOD patients and the second reference value indicates the average amplitude of the EEG signal when entering the anesthetic-induced loss of consciousness in a plurality of POD patients. These reference values were determined beforehand in groups of POD patients and nonPOD patients.

If, for example, the second reference value is greater than the first reference value by a specific factor, for example by a factor of 3, the preset amount is exceeded.

In this case, in step 706 a corresponding piece of information is provided as a parameter indicatively indicating that postoperative delirium has occurred. This information is then used by a doctor or anesthetist in step 707. For example, the doctor or anesthetist can use this information to produce a shallower state of anesthesia on the basis of additional parameters of the patient and/or take supportive therapeutic measures directly after the anesthetic is administered that counteract the development of postoperative delirium.

In order to carry out the method according to FIGS. 4, 5 and 7, an EEG-based brain function monitor or a computer in general can be used. The method steps for determining the intraoperative alpha peak frequency and for carrying out the comparison with the reference value (FIG. 3) or for determining the power of the alpha band of the EEG signal and for carrying out the check to see whether an increase in the power of the alpha band from the first power to the second power is below a predefined amount, or to determine the curve of the average amplitude of the "direct current" EEG signal and to evaluate the curve are carried out in this case by a program code that is executed in a processor. The program code is stored in a memory of the processor or is loaded thereon before being executed. The processor that carries out the program code can be the main processor of the EEG monitor or a separate processor.

FIG. 7 shows, by way of example, a possible way of implementing such an EEG-based brain function monitor 1. The EEG monitor 1 comprises a microprocessor 2, a memory 3, a control apparatus 4, an output unit 5 and an interface 7 for connecting EEG cables.

By means of the interface 7, EEG cables comprising EEG electrodes 61, 62 can be connected to the EEG monitor 1. Two EEG cables are shown by way of example, which pick up an EEG signal, it being possible for additional EEG cables to be provided for picking up a multi-channel EEG signal.

The EEG signal is supplied to the microprocessor 2. The program code is stored in the memory 3 or a program code can be loaded in the memory 3 that carries out the method explained with reference to FIG. 4 and/or the method explained with reference to FIG. 5 and/or the method explained with reference to FIG. 7 when executed in the microprocessor 2. By means of the control apparatus 4, the procedure can be controlled and this can be set up to obtain corresponding input instructions. In this case, the control apparatus 4 can be or contain a main processor of the EEG monitor 1. Alternatively, the functionality of the microprocessor 2 can be taken over by the control apparatus 4. By means of the control apparatus 4 and/or additional modules (not shown), additional functionalities of the EEG monitor 1 can be implemented in this case.

When executing the loaded program code, the microprocessor 2 therefore determines the intraoperative alpha peak frequency, compares it with a reference value and determines whether the intraoperative alpha peak frequency determined is significantly lower than a preset reference value for the alpha peak frequency. The corresponding information is transmitted to the output unit 5 and output thereon. This can be done by means of a monitor 51 and/or an acoustic unit 52, for example.

When carrying out the loaded program code, the microprocessor 2 alternatively or additionally evaluates the power in the alpha band according to FIG. 5. In this case, a check is made to see whether an increase in the power of the alpha band from the preoperative power to the intraoperative power is below a predefined amount. The corresponding information is transmitted to the output unit 5 and output thereon. This can be done by means of the monitor 51 and/or the acoustic unit 52.

Alternatively or in addition, when carrying out the loaded program code, the microprocessor 2 evaluates the curve of the average amplitude of the "direct current" EEG signal according to FIG. 7. In this case, a check is made to see whether the increase in the average amplitude of the EEG signal is above a predefined amount when entering the anesthetic-induced loss of consciousness. The corresponding information is transmitted to the output unit 5 and output thereon. This can be done by means of the monitor 51 and/or the acoustic unit 52.

It goes without saying that the invention is not restricted to the above-described embodiments and various modifications and improvements may be made without departing from the concepts described here. Any of the features may be used separately or in combination with any other features, provided that they are not mutually exclusive, and the disclosure extends to, and includes, all combinations and sub-combinations of one or more features described here. If and when ranges are defined, these therefore include all the values within these ranges and all sub-ranges included in a range.

The invention claimed is:

1. A method for providing a parameter that indicates a heightened likelihood of postoperative delirium occurring, wherein the method comprises:
   receiving at least one electroencephalography (EEG) signal from a head of a patient, wherein the at least one EEG signal is received within a period of time in which the patient is under anesthesia;
   filtering the at least one EEG signal to produce at least one filtered EEG signal, wherein the at least one filtered EEG signal comprises a reduced total amount of frequencies compared to a total amount of frequencies of the at least one EEG signal;

determining an intraoperative alpha peak frequency of the at least one filtered EEG signal, wherein the intraoperative alpha peak frequency is a frequency in an alpha band of the at least one filtered EEG signal at which a power is greatest;

determining a difference value between the intraoperative alpha peak frequency and a preset reference value associated with the heightened likelihood of postoperative delirium; and providing the parameter that indicates the heightened likelihood of postoperative delirium occurring based on the difference value being greater than a preset difference value.

2. The method of claim 1, wherein the preset reference value is established by averaging a plurality of intraoperative alpha peak frequencies measured in a plurality of patients who have not developed postoperative delirium.

3. The method of claim 1, wherein the preset reference value is dependent on an age bracket of the patient.

4. The method of claim 1, wherein the intraoperative alpha peak frequency is determined at a point in time at which the patient is in a stable state of anesthesia.

5. The method of claim 1, wherein the parameter is provided when the difference value between the preset reference value and the intraoperative alpha peak frequency exceeds a defined percentage deviation from the preset reference value or a defined absolute difference between the intraoperative alpha peak frequency and the preset reference value.

6. The method of claim 1, wherein the at least one EEG signal comprises a plurality of frontal EEG signals, and wherein the plurality of frontal EEG signals is averaged in order to determine the intraoperative alpha peak frequency.

7. The method of claim 1, wherein the intraoperative alpha peak frequency is the frequency within the alpha band and a theta band of the at least one filtered EEG signal at which the power is greatest, and wherein the power is within a power spectrum of the at least one filtered EEG signal.

8. The method of claim 1, further comprising:
determining an additional power of the alpha band of the at least one filtered EEG signal, the additional power of the alpha band associated with a power spectrum of the at least one filtered EEG signal and being defined as an integral of a plurality of powers across all frequencies in the alpha band, a first power of the alpha band being determined at a preoperative point in time before an anesthetic-inducing medicine is administered to the patient, and a second power of the alpha band being determined at an intraoperative point in time after the patient enters anesthetic-induced loss of consciousness;

determining whether a power increase between the first power and the second power is below a predefined amount; and providing the parameter that indicates the heightened likelihood of postoperative delirium occurring based on determining the power increase is below the predefined amount.

9. The method of claim 1, wherein at least a portion of the method is performed using a computer executing a computer program comprising a program code for carrying out at least a portion of the method according to claim 1.

10. A method for providing a parameter that indicates a heightened likelihood of postoperative delirium occurring, wherein the method comprises:
receiving a first electroencephalography (EEG) signal from a head of a patient, wherein the first EEG signal is received at a preoperative point in time before an anesthetic-inducing medicine is administered to the patient;

receiving a second EEG signal from the head of the patient, wherein the second EEG signal is received at an intraoperative point in time after the patient has entered an anesthetic-induced loss of consciousness;

filtering the first EEG signal to produce a first filtered EEG signal, and filtering the second EEG signal to produce a second filtered EEG signal, wherein each of the first and second filtered EEG signals comprises a reduced total amount of frequencies compared to a total amount of frequencies of the first and second EEG signals, respectively;

determining a first power of an alpha band of the first filtered EEG signal based on an integral of a first plurality of powers across all frequencies in the alpha band;

determining a second power of the alpha band of the second filtered EEG signal based on an integral of a second plurality of powers across all frequencies in the alpha band;

determining whether a power increase between the first power and the second power is below a predefined amount associated with the heightened likelihood of postoperative delirium; and providing the parameter indicating the heightened likelihood of postoperative delirium occurring based on determining the power increase is below the predefined amount.

11. The method of claim 10, wherein the predefined amount is determined based on a relationship between a first power increase and a second power increase, and
wherein the first power increase is between a first average of powers of a first plurality of filtered EEG signals received at the preoperative point in time for a first plurality of patients that have not developed postoperative delirium and a second average of powers of a second plurality of filtered EEG signals received at the intraoperative point in time for the first plurality of patients, and
wherein the second power increase is between a third average of powers of a third plurality of filtered EEG signals received at the preoperative point in time for a second plurality of patients that have developed postoperative delirium and a fourth average of powers of a fourth plurality of filtered EEG signals received at the intraoperative point in time for the second plurality of patients.

12. The method of claim 11, wherein the predefined amount is created by a difference between the first power increase and the second power increase minus a percentage or absolute tolerance value.

13. The method of claim 10, wherein the predefined amount is determined based on an age bracket of the patient.

14. The method of claim 10, wherein the parameter is provided based on the power increase from the first power to the second power being below 15 dB.

15. The method of claim 10, wherein the first EEG signal and the second EEG signal each comprise a frontal EEG signal.

16. The method of claim 10, comprising using machine-learning techniques to determine whether the power increase between the first power and the second power is below the predefined amount.

17. A device for providing a parameter that indicates a heightened likelihood of postoperative delirium occurring, wherein the device comprises:
- a sensor to receive at least one electroencephalography (EEG) signal from a head of a patient, wherein the at least one EEG signal is recorded within a period of time in which the patient is under anesthesia;
- a filter to filter the at least one EEG signal to produce at least one filtered EEG signal, wherein the at least one filtered EEG signal comprises a reduced total amount of frequencies compared to a total amount of frequencies of the at least one EEG signal; and
- a processor to:
  - determine an intraoperative alpha peak frequency of the at least one filtered EEG signal, wherein the intraoperative alpha peak frequency is a frequency in an alpha band of a power spectrum of the at least one filtered EEG signal at which a power is greatest;
  - determine a difference value between the intraoperative alpha peak frequency and a preset reference value associated with the heightened likelihood of postoperative delirium; and
  - provide the parameter that indicates a heightened likelihood of postoperative delirium occurring based on the difference value being greater than a preset difference value.

18. The device of claim 17, wherein the preset reference value is determined by averaging a plurality of intraoperative alpha peak frequencies measured for a plurality of patients that have not developed postoperative delirium.

19. The device of claim 17, wherein the processor determines the intraoperative alpha peak frequency at a point in time at which the patient is in a stable state of anesthesia.

20. The device of claim 17, comprising a plurality of sensors to receive a plurality of frontal EEG signals for the patient, and wherein the plurality of frontal EEG signals are averaged to determine the intraoperative alpha peak frequency.

* * * * *